United States Patent
Broersma

(10) Patent No.: US 6,590,663 B1
(45) Date of Patent: Jul. 8, 2003

(54) REFLECTOMETER

(75) Inventor: Harmen Broersma, Amsterdam (NL)

(73) Assignee: Spectrostar B.V., Amsterdam (NL)

( * ) Notice: Subject to any disclaimer, the term of this patent is extended or adjusted under 35 U.S.C. 154(b) by 0 days.

(21) Appl. No.: 09/890,165

(22) PCT Filed: Dec. 16, 1999

(86) PCT No.: PCT/NL99/00777

§ 371 (c)(1),
(2), (4) Date: Jan. 25, 2002

(87) PCT Pub. No.: WO00/45151

PCT Pub. Date: Aug. 3, 2000

(30) Foreign Application Priority Data

Jan. 27, 1999 (NL) ............................................. 1011147

(51) Int. Cl.[7] ......................... G01N 21/47; G01N 21/55; G02B 6/04; F21V 7/04
(52) U.S. Cl. ............... 356/445; 356/238.1; 250/227.29; 362/551
(58) Field of Search .................. 356/445, 446, 356/237.1, 238.1, 425; 250/227.29; 362/31, 551, 554, 556, 558

(56) References Cited

U.S. PATENT DOCUMENTS

| | | | | |
|---|---|---|---|---|
| 4,464,054 A | * | 8/1984 | Karras et al. | 356/446 |
| 4,518,259 A | | 5/1985 | Ward | |
| 4,991,971 A | * | 2/1991 | Geary et al. | 356/446 |
| 5,640,246 A | * | 6/1997 | Castonguay | 356/445 |
| 5,754,283 A | * | 5/1998 | Keane et al. | 356/446 |
| 5,796,472 A | | 8/1998 | Wirthlin | |

FOREIGN PATENT DOCUMENTS

| | | |
|---|---|---|
| WO | WO 96/13709 | 5/1996 |
| WO | WO 97/41421 | 11/1997 |

* cited by examiner

*Primary Examiner*—Alan A. Mathews
(74) *Attorney, Agent, or Firm*—Swanson & Bratschun, L.L.C.

(57) ABSTRACT

A reflectometer, comprising an illuminator in a 45°/0° configuration with a light source formed by a lamp and an illuminator optic. Light emitted by the lamp is passed after reflection via a measuring opening into a housing and supplied to a measuring system contained therein. Furthermore, the illuminator optic is formed by a number of light guides which start at the light source and end in the form of a rim with a conoidal emission side. The light guides form one or several groups, a group of light guides being made in one piece of plastic.

14 Claims, 5 Drawing Sheets

REFLECTOMETER

RELATED APPLICATIONS

This application is a 35 U.S.C. § 371 national phase application of PCT/NL99/00777 (WO 00/45151) filed on Dec. 16, 1999, entitled "Reflectometer," which claims priority to the Netherlands Application Number 1011147, filed Jan. 27, 1999.

The present invention relates to a reflectometer, comprising an illuminator in a 45°/0° configuration with a light source formed by a lamp and an illuminator optic, light emitted by the lamp being passed after reflection via a measuring opening into a housing and supplied to a measuring system contained therein, and the illuminator optic being formed by a number of light guides which start at the light source and end in the form of a rim with a conoidal emission side. More in particular, the invention relates to a reflectometer used in a construction as spectrophotometer, in which the measuring system can be conventionally formed by a spectrophotometer system with dispersion means, optical components cooperating therewith, and detection means.

Such a reflectometer is known from the international patent application WO 96/13709. For the illuminator in such a reflectometer designed as spectrophotometer, ISO standards have been set up; with respect to the measuring geometry for a reflection measurement the most recent ISO standards for color measurement, namely ISO-5-4:1995(E), give the 45°/0° configuration, in which in the annular influx mode the illumination has to be effected on all sides at an angle of 45 (±5)° and the reflection measurement at 0 (±5)°.

It is known to realize an illumination on all sides at an angle of 45° by means of one or more lamps or LED's which, provided or not provided with a lens, are directed from different directions to a specimen to be exposed. To comply with the most recent ISO standards, however, this requires a large number of lamps, which makes the construction of the spectrophotometer relatively expensive. It is also known to use one or more light sources in a diffusion chamber, the light radiating to the specimen at 45° via an annular opening. The drawback of this solution is that such a diffusion chamber occupies relatively much space, which adversely affects the cost price and the dimensions of the spectrophotometer. Furthermore, U.S. Pat. No. 4,320,442 discloses an annular illuminator in which a system of reflectors is used, which are rather complicated owing to their shape. In the spectrophotometer as described in the opening paragraph, use is made of an illuminator in which the illuminator optic is formed by a number of optical guides which start at a light source and end in the form of a rim with a conoidal emission side. Such a spectrophotometer is known from U.S. Pat. No. 4,464,054. In the manufacture thereof, a rather labor-intensive finishing and mounting of a plurality of light guides in the form of glass fibers is necessary, both on the side of the light source and on the conoidal emission side.

The object of the invention is to provide the spectrophotometer with an illuminator optic which can be made in a simple and relatively inexpensive manner, and which illuminator optic also complies with the above-mentioned ISO standards.

According to the invention the reflectometer as described in the opening paragraph is characterized in that the illuminator optic consists of one group or of several groups of light guides, a group of light guides being made in one piece of plastic, said one piece having an entrance area, a transition area for gradually merging the entrance area into a number of mechanically separated light guides and an annular emission area in which the light guides are mechanically connected with each other. This solution enables inexpensive mass production of the illuminator optic, in particular by using injection molding techniques. It may be noticed that from U.S. Pat. No. 4,518,259 an illuminator optic, made from plastic, is known per se.

The illuminator optic is based on the principle of total internal reflection in the light guides; as a result of the difference ill refractive index with the surrounding air. This ensures that light radiated in can be transported practically without losses, as long as the geometric conditions for total reflection remain satisfied. In connection therewith, it is important that the illuminator optic contacts the further housing of the spectrophotometer in as few places as possible.

In connection with the geometric conditions imposed on the light guides, the composition of the material of the light guides, their thickness and curvature are adjusted to the angles at which light can enter the glass guides in such a manner that the requirements for total internal reflection are nearly completely satisfied.

For each group of light guides a lamp could be present. From considerations of cost, however, it is preferred to make use of only one lamp. Similarly, it is preferred if the illuminator optic is formed by only one group of light guides. The illuminator optic may then be formed by, for instance, one single injection molded part.

Preferably, the lamp is rigidly connected with the illuminator optic. Not only does this result in a saving of mounting cost, but an accurately positioned fastening method for the lamp with respect to the illuminator optic is obtained. The lamp can be directly attached to the illuminator with optically bright cement, thereby excluding both light losses through reflections and through possible soiling and alignment errors, while, furthermore, the stability of the light intensity radiated in becomes insensitive to unintentional displacement of the lamp. When using a separate lamp foot or supporting construction, displacements can be caused by, for instance, vibrations and warming up.

In a preferred embodiment the lamp is formed by a Xenon flash tube. Such tubes have advantages over the light bulbs frequently used in known spectrophotometers. The emitted light properly corresponds with daylight, while light bulbs contrarily have very little blue light and even less UV-radiation. In particular if the detection means are provided with silicon photodiodes, which actually have a low sensitivity to short wavelengths, in particular blue light and UV-radiation, Xenon flash tubes form an ideal light source. The cost price is low and the light output is high. If the flash power is properly selected, the life can be tens of millions of pulses. The diffuse light from a Xenon tube, however, cannot be simply directed to a specimen, while through their dimensions and shape and the required high-voltage feed they cannot be simply arranged close to a specimen either. To comply with the above-mentioned "annular 45°/0° ISO standard", diffusion chambers, various reflectors and so-called integrating spheres were used in the past. All these solutions, however, are relatively expensive and occupy much space, with the result that a Xenon illumination is particularly used in larger and more expensive apparatus. The illuminator optic according to the invention, however, offers a solution for the use of Xenon flashlight which occupies little space and, moreover, can be made and arranged at low cost. The possibilities of the illuminator optic, however, are not limited to the combination with a Xenon tube. Also when using it with other sources, tubular or not tubular, a high illumination output can be obtained for an "annular 45°/0°" illumination with a form of the entrance area adapted to the light source, while only one light source is required or one LED of each color to be used.

The lamp is preferably tubular and completely surrounded by a reflector with the exception of a slit on the side of the entrance area of the illuminator optic. The Xenon tube may, as already mentioned, be glued to the entrance side of the illuminator optic. By further surrounding the lamp by a reflector, it is achieved that as little light as possible is emitted in directions other than to the illuminator optic.

In a specific design the light entrance of the entrance area of the illuminator optic has a rectangular cross-section with a thickness greater than that of the channels. The transition area following the light entrance provides a conical course, the channels, with decreasing thickness of the entrance area, being formed from the rectangular cross-section while diverging widthwise. This design of the transition area, in which the thickness of the entrance area decreases according as the width of the beam of rays increases, efficiently couples the shape of the light source to these light channels, which first diverge groupwise and then support each other in other combinations in some places. These contact areas serve to give the construction sufficient strength, so that the illuminator optic can be manufactured reliably and at low cost. The contact areas have been selected in combination with the angles of flexure of the channels in such a manner with respect to the effective optical width of the channels that the light is gradually deflected everywhere and the conditions of total reflection are satisfied as much as possible. This prevents too much light exit and maximizes the efficiency.

It is necessary for the firmness of the illuminator optic to interconnect the channels at the exit. In the emission area this causes a light scattering from the end of the channels. It has been found that the diffuse light can be concentrated somewhat on the site in the direction of the specimen by giving the ends of the channels a convex lens-shaped design.

The light emitted via the exits of the channels is conoidally directed at an angle of 45°, and the thickness of the lens-shaped exit openings of the channels, measured perpendicularly to the light direction, is less than 17.5% of the distance from the exit of the channels to the center of the exposed surface.

The illuminator optic is made of an optically bright plastic, preferably acrylate glass (PMMA).

It has been found that the intensity of the scattered light from the illuminator optic is representative of the intensity of the reflected light. To enable allowance for variations therein and for the effect of these variations on the final measuring results, detection means are arranged near the illuminator optic to measure the scattered light from the illuminator optic and, in dependence thereon, to make corrections to the measuring results given by the measuring system. The detection means are formed by a diffuser and a photodetector and, because the scattered light is most intense where the channels are most curved, are arranged near the most curved parts of the illuminator optic.

The reflectometer according to the invention is an inexpensive, handy and reliable instrument for measuring surface colors of printing matter, paint, plastics, textiles, foodstuffs, etc. The measuring system, in particular the spectrophotometer system, can be connected to a computer so as to be able to process the information from this measuring system.

The invention will now be explained in more detail with reference to the accompanying drawings, in which.

Although the reflectometer is not limited in its use to a spectrophotometer, but can also be used in reflection densitometers and reflection colorimeters of the tristimulus type, the use in a spectrophotometer will be described in the present exemplary embodiment.

Figure 1:
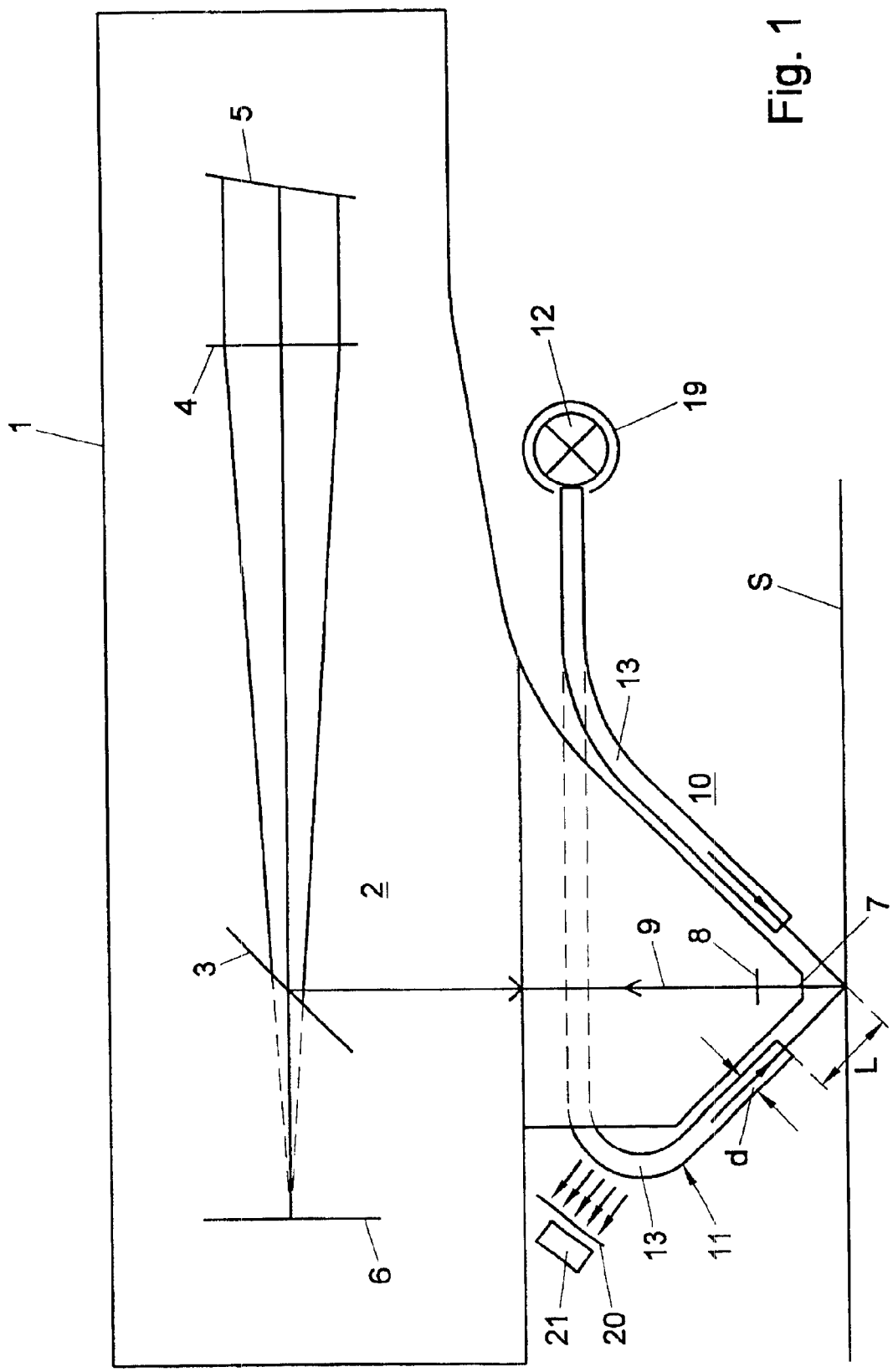
FIG. 1 shows a schematic structure of a reflectometer according to the invention with a spectrophotometer system in a Littrow arrangement.

The reflectometer shown in FIG. 1 comprises a housing 1, which contains a spectrophotometer system 2 in a Littrow arrangement with a reflecting element 3, a collimator lens 4, a grating monochromator 5, and a detector 6. Since such a measuring system is known from E. G. Loewen, E. Popov; *Diffraction gratings and applications* (Marcel Dekker, Inc., New York, 1997), see in particular paragraph 12.5, the operation of this system needs no further discussion. The invention only relates to the manner in which, via an entrance opening 7 and a lens 8, a substantially parallel beam 9 reflected by a specimen S is obtained and not to the spectrophotometer system itself In principle, this measuring system can be designed in all kinds of known manners and is therefore certainly not limited to the Littrow arrangement described herein.

The reflectometer comprises an illuminator 10 with an illuminator optic 11 and a lamp 12. The illuminator optic is formed by light guides 13 which start at the lamp 12 and end in the form of a rim with a conoidal emission side. In accordance with the current ISO standards, the surface of the specimen S to be exposed is irradiated at an angle of 45°, while at most a tolerance of ±5° occurs. Of the light scattered and reflected by the specimen surface, a beam of light 9 is passed perpendicularly to this surface via the opening 7 with the lens 8 to the measuring system 2. The lens 8 is of such design that the tolerance in the direction of radiation of the beam 9 is also at most ±5°.

Figure 2:
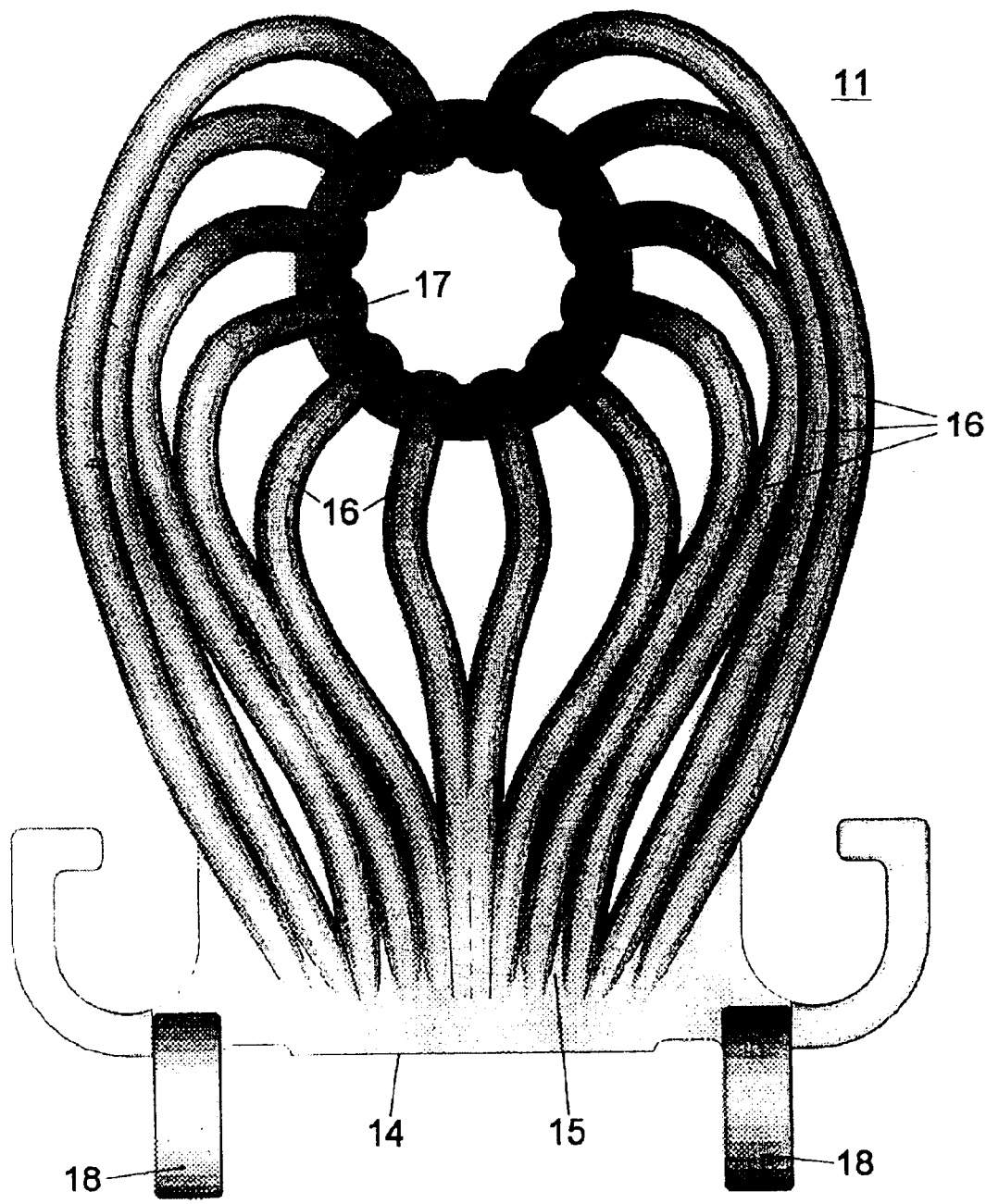
FIG. 2 is a bottom view of the illuminator optic therein.
Figure 3:
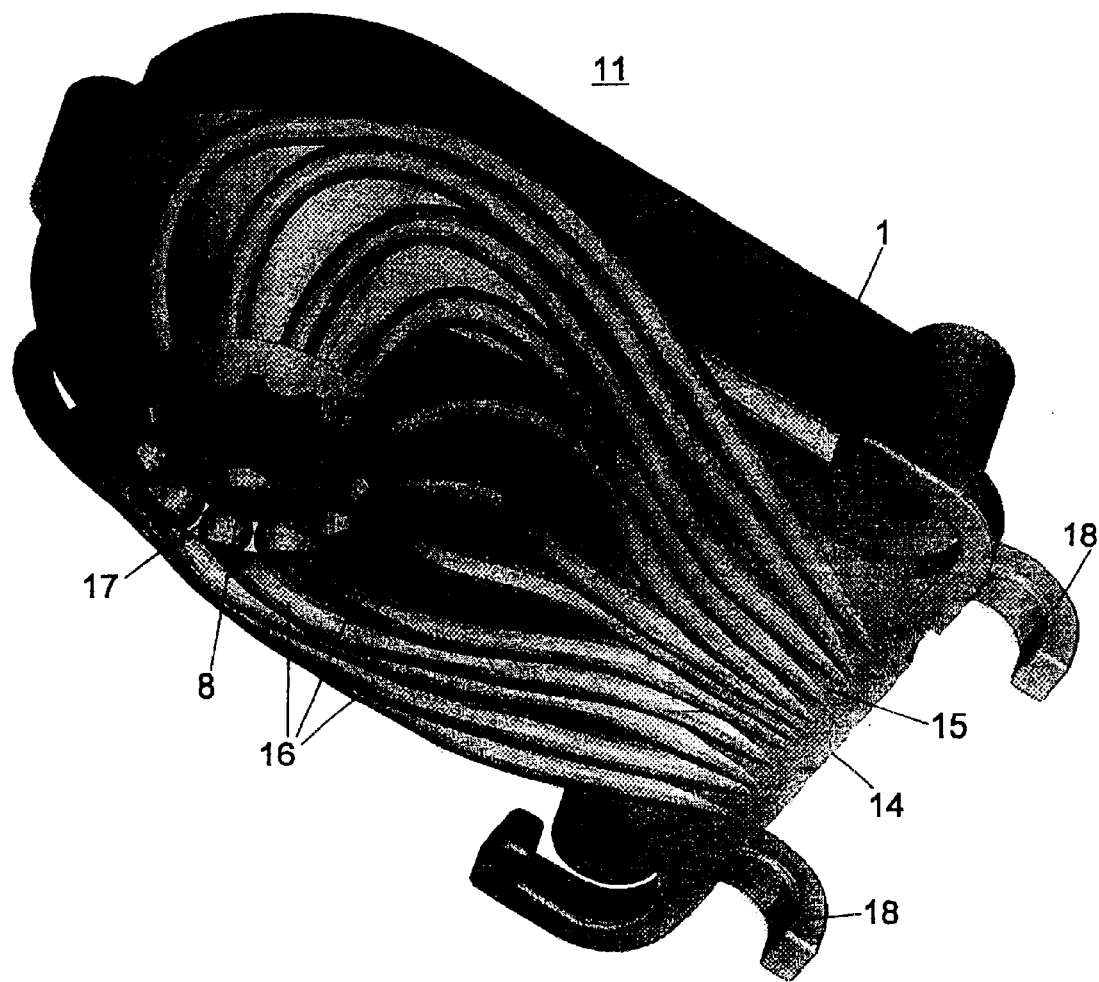
FIG. 3 is a perspective view of the illuminator optic.

A practical example of an illuminator optic 11 according to the invention is in particular shown in FIGS. 2 and 3. In this embodiment the illuminator optic consists of one group of light guides which is made in one piece of an optically bright plastic, in particular acrylate glass. This group of light guides consists of an entrance area 14 which, via a transition area 15, gradually merges into a number of light channels 16 and an annular emission area 17, in which the channels 16 are interconnected again. Near the entrance area 14 the illuminator optic 11 is provided with fastening elements 18, which are co-molded in the manufacture of the illuminator optic 11. Between these fastening elements 18 the lamp 12 is rigidly arranged, in particular cemented. The light entrance of the entrance area 14 has an elongated rectangular cross-section, the thickness of which is greater than that of the channels 16. The transition area 15 following the light entrance provides a conical course, the channels, with decreasing thickness of the entrance area, being formed from the rectangular cross-section while diverging widthwise. From the transition area 15 the channels diverge groupwise and support each other again in other combinations. In the annular emission area 17, where the channels 16 are all interconnected again, the ends of the channels are of a convex lens-shaped design. Through the composition of the material of the light guides 13, in particular the refractive index of the material, and the adjustment of their thickness and curvature to the angles at which light can enter the light guides 13, the requirements for total internal reflection are satisfied nearly completely, so that practically all the incoming light exits via the lens-shaped exit openings of the channels. The light emitted via these ends is conically directed completely and uniformly on all sides at an angle of 45°. The thickness d of the lens-shaped exit openings of the channels 16, measured perpendicularly to the light direction, is less than 17.5% of the distance L from the exit of the channels to the center of the exposed surface. The thickness of the lens-shaped exit openings need not correspond to the thickness of the channels; they may be slightly thicker and gradually become thinner toward the end, or they may have a constant thickness, but have tapering lens-shaped ends.

As lamp 12 a Xenon flash tube is used, which, as mentioned above, is cemented to the fastening elements 18. Provided around this lamp 12 is a reflector 19, which leaves a slit-shaped opening clear on the side of the entrance area 14 of the illuminator optic.

As indicated above, the channels are formed such that only a minimum amount of light exits therefrom as a result of the fact that the requirements of total reflection can never be satisfied completely. The intensity of this scattered light produced by the illuminator is found to be accurately representative of the light intensity falling on the specimen S. To enable measurement of this scattered light, a diffuser 20 and a measuring cell 21 in the form of a reference photodiode is placed near the greatest curvature in the channels. The measurement of the scattered light by means of this measuring cell enables fluctuations in the light intensity to be corrected with software. Such fluctuations may be caused by, inter alia, variations in the integrated total light intensity of the flash tube and/or because the discharge in the flash tube has no exactly fixed position, as is the case with, for instance, an incandescent filament. For the last-mentioned reason the geometry of the radiation into the illuminator may differ from flash to flash, which causes additional light intensity variations on the specimen S.

Figure 4:
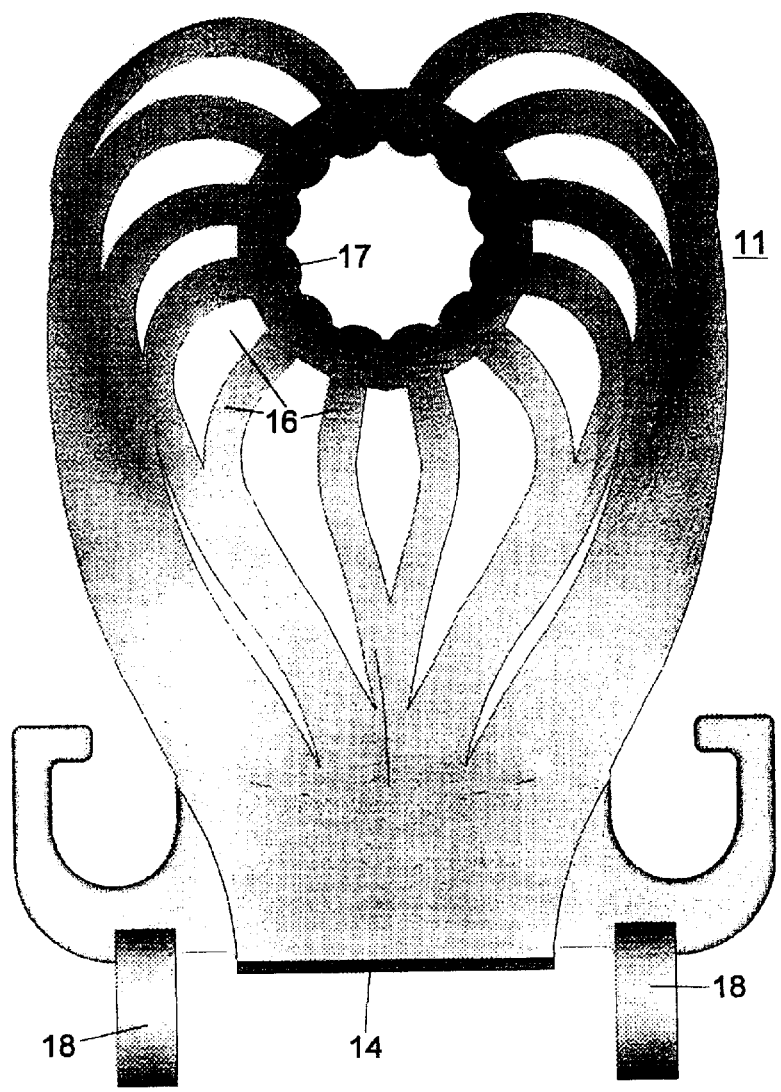
FIG. 4 is a top plan view of the illuminator optic in a second embodiment.
Figure 5:
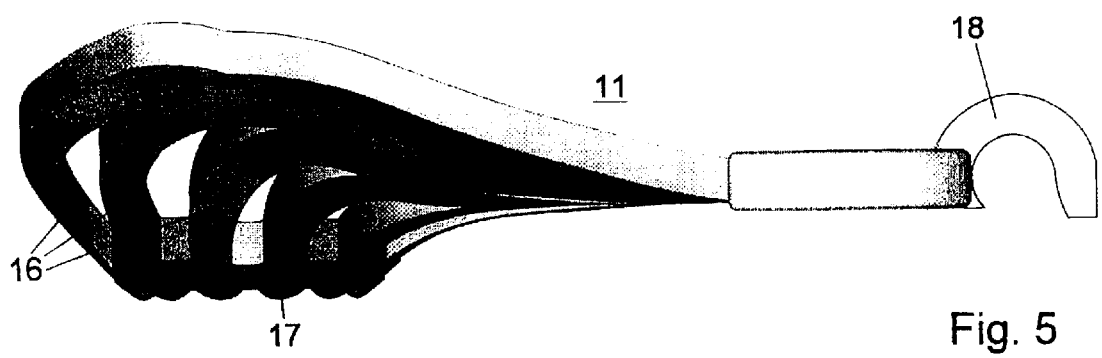
FIG. 5 is a side view of the illuminator optic in FIG. 4.
Figure 6:
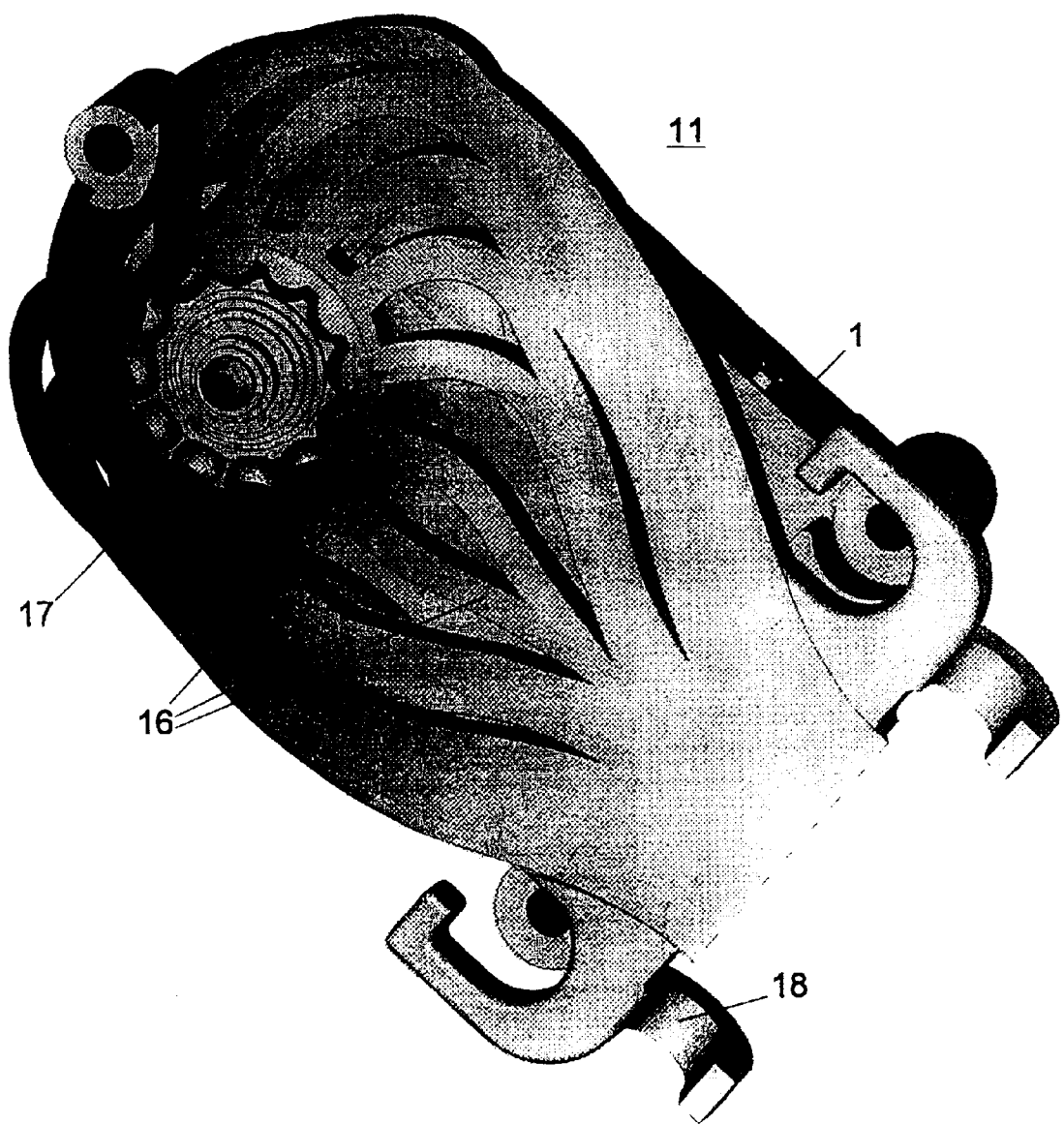
FIG. 6 is a perspective view of the last-mentioned illuminator optic, attached at the bottom of the housing.

FIGS. 4–6 show a second exemplary embodiment of an illuminator optic according to the invention.

Although the structure of this illuminator optic largely corresponds with that of FIGS. 2 and 3, the channels 16 have a practically square cross-section, and the illuminator optic is manufactured in a different manner. The light guides are formed herein by making recesses in a corrugated plate of acrylate. This may be done by compression or injection molding.

The invention is not limited to the exemplary embodiment described herein with reference to the drawing, but comprises all kinds of modifications, of course as far as falling within the scope of protection of the appended claims.

In particular, it is pointed out that the illuminator optic may consist of several individually molded parts, but which are of such design that they are adapted to each other so as to obtain a uniformly circumferential illumination conoid. If, for instance, the illuminator optic consists of two of such parts, that is to say two groups of light guides, of which each part is molded in one piece, then two lamps may be present as well. Although it is not recommendable from a viewpoint of manufacturing technique, a distribution of the light guides over several individual groups is possible.

In another embodiment it is possible to make use of only one lamp indeed, yet allowing a group of light guides to extend from two sides to one single annular emission area.

What is claimed is:

1. A reflectometer, comprising an illuminator in a 45°/0° configuration with a light source formed by a lamp and an illuminator optic, light emitted by the lamp being passed after reflection via a measuring opening into a housing and supplied to a measuring system contained therein, and the illuminator optic being formed by a number of light guides which start at the light source and end in the form of a rim with a conoidal emission side, characterized in that the illuminator optic consists of one group or of several groups of light guides, a group of light guides being made in one piece of plastic, said one piece having an entrance area, a transition area for gradually merging the entrance area into a number of mechanically separated light guides and an annular emission area in which the light guides are mechanically connected with each other.

2. The reflectometer according to claim 1, characterized in that the composition of the material of the light guides, their thickness and curvature are adjusted to the angles at which light can enter the light guides in such a manner that the requirements for total internal reflection are nearly completely satisfied.

3. The reflectometer according to claim 1, characterized in that the illuminator optic contains one group of light guides and one lamp.

4. The reflectometer according to claim 3, characterized in that the lamp is rigidly connected with the illuminator optic.

5. The reflectometer according to claim 3, characterized in that the lamp is formed by a Xenon flash tube.

6. The reflectometer according to claim 2, characterized in that the lamp is tubular and completely surrounded by a reflector with the exception of a slit on the side of the entrance area of the illuminator optic.

7. The reflectometer according to claim 2, characterized in that the light entrance of the entrance area of the illuminator optic has a rectangular cross-section greater than that of the light guides in the transition area.

8. The reflectometer according to claim 7, characterized in that the transition area following the light entrance provides a conical course, the light guides, with decreasing cross-section of the entrance area, being formed from the rectangular cross-section while diverging widthwise.

9. The reflectometer according to claim 2, characterized in that from the transition area the light guides diverge groupwise, while at least a number of them support each other in different places.

10. The reflectometer according to claim 2, characterized in that in the annular emission area the ends of the light guides are of a convex lens-shaped design.

11. The reflectometer according to claim 2, characterized in that the light emitted via the exits of the light guides is conoidally directed at an angle of 45°, and the thickness of the lens-shaped exit openings of the light guides, measured perpendicularly to the light direction, is less than 17.5% of the distance from the exit of the light guides to the point where the light beams coming out of the light guides cross each other.

12. The reflectometer according to claim 1, characterized in that the illuminator optic is made of an optically bright plastic, preferably acrylate glass.

13. The reflectometer according to claim 1, characterized in that near the illuminator optic detection means are arranged to measure the scattered light from the illuminator optic and, in dependence thereon, to make corrections to the measuring results given by the measuring system.

14. The reflectometer according to claim 13, characterized in that the detection means are arranged near the most curved parts of the illuminator optic and are formed by a diffuser and a photodetector.

* * * * *